(12) United States Patent
Yuan et al.

(10) Patent No.: US 10,470,711 B2
(45) Date of Patent: Nov. 12, 2019

(54) ELECTRONIC SENSOR SYSTEM FOR USE WITH FOOTWEAR

(71) Applicant: WIIVV WEARABLES INC., Vancouver (CA)

(72) Inventors: Kaiwen Yuan, Richmond (CA); Manuj Aggarwal, Vancouver (CA); Colin Michael Lawson, Vancouver (CA); Enger Lasada Bewza, Surrey (CA); Shamil Mahendra Hargovan, San Jose, CA (US); Louis-Victor Jadavji, West Vancouver (CA)

(73) Assignee: Wiivv Wearables Inc., Vancouver (CA)

( * ) Notice: Subject to any disclaimer, the term of this patent is extended or adjusted under 35 U.S.C. 154(b) by 193 days.

(21) Appl. No.: 15/224,390

(22) Filed: Jul. 29, 2016

(65) Prior Publication Data

US 2017/0027512 A1 Feb. 2, 2017

Related U.S. Application Data

(60) Provisional application No. 62/199,818, filed on Jul. 31, 2015.

(51) Int. Cl.
*A61B 5/00* (2006.01)
*A61B 5/0205* (2006.01)
(Continued)

(52) U.S. Cl.
CPC .......... *A61B 5/6829* (2013.01); *A43B 3/0005* (2013.01); *A43B 17/006* (2013.01);
(Continued)

(58) Field of Classification Search
CPC .......... G01S 19/19; G01S 19/13; A63F 13/21; A63F 13/212; A63F 13/216;
(Continued)

(56) References Cited

U.S. PATENT DOCUMENTS

| 4,745,930 A | 5/1988 | Confer |
| 5,505,072 A * | 4/1996 | Oreper .................... G01L 1/205 |
| | | 702/116 |

(Continued)

FOREIGN PATENT DOCUMENTS

| CN | 101828794 A | 9/2010 |
| WO | 2013/126751 A1 | 8/2013 |

OTHER PUBLICATIONS

Weiss, C.C., 2014, "Moticon Sensor Insoles Track Your Feet for Injury and Performance," website: http://newatlas.com/moticon-sensor-insoles/30920/. [retrieved on Feb. 9, 2017], 5 pages.

(Continued)

*Primary Examiner* — Rex R Holmes
(74) *Attorney, Agent, or Firm* — Perkins Coie LLP; Jordan Becker

(57) ABSTRACT

The disclosed technique relates to an insert for footwear and to a composite orthotic insole comprising said insert, wherein the insert is embedded with a plurality of force (or pressure) sensors, and may be used to provide feedback on important information regarding the wearer's gait biomechanics. The layer of sensors may be used to assist in monitoring the wearer's health via foot pressure tracking. The insole can use a relative large number of sensors, which together provide broad coverage of the human foot impact area.

25 Claims, 10 Drawing Sheets

(51) Int. Cl.
*A61B 5/024* (2006.01)
*A61B 5/103* (2006.01)
*A43B 17/00* (2006.01)
*A43B 3/00* (2006.01)
*A63F 13/211* (2014.01)
*A63F 13/216* (2014.01)
*A63F 13/212* (2014.01)
*A63F 13/65* (2014.01)
*H04Q 9/00* (2006.01)
*G01S 19/13* (2010.01)
*G01S 19/19* (2010.01)
*A63F 13/21* (2014.01)
*A61B 5/11* (2006.01)

(52) U.S. Cl.
CPC ...... *A61B 5/02055* (2013.01); *A61B 5/02438* (2013.01); *A61B 5/02444* (2013.01); *A61B 5/1038* (2013.01); *A63F 13/21* (2014.09); *A63F 13/211* (2014.09); *A63F 13/212* (2014.09); *A63F 13/216* (2014.09); *A63F 13/65* (2014.09); *G01S 19/13* (2013.01); *G01S 19/19* (2013.01); *H04Q 9/00* (2013.01); *A61B 5/112* (2013.01); *A61B 5/6807* (2013.01); *A61B 5/6812* (2013.01); *A61B 2562/0247* (2013.01); *A61B 2562/046* (2013.01); *A63F 2300/8082* (2013.01); *H04Q 2209/43* (2013.01); *H04Q 2209/86* (2013.01)

(58) Field of Classification Search
CPC ......... A63F 13/211; A63F 13/65; H04Q 9/00; A61B 5/6829; A61B 5/02438; A61B 5/02444; A61B 5/1038; A61B 5/02; A43B 3/0005; A43B 17/006
See application file for complete search history.

(56) References Cited

U.S. PATENT DOCUMENTS

| | | | |
|---|---|---|---|
| 6,195,921 | B1 | 3/2001 | Truong |
| 7,587,937 | B2 | 9/2009 | Haselhurst et al. |
| 7,998,092 | B2 | 8/2011 | Avni et al. |
| 9,743,861 | B2* | 8/2017 | Giedwoyn ............. A61B 5/112 |
| 2001/0011496 | A1 | 8/2001 | Mishima et al. |
| 2002/0121146 | A1 | 9/2002 | Manaresi et al. |
| 2010/0170704 | A1* | 7/2010 | Yang .................... H01H 13/704 174/254 |
| 2013/0079693 | A1 | 3/2013 | Ranky et al. |
| 2014/0200834 | A1 | 7/2014 | Ross |
| 2015/0330855 | A1* | 11/2015 | Daniecki .............. A43B 3/0005 73/727 |

OTHER PUBLICATIONS

International Search Report and Written Opinion PCT/US2016/045047 dated Dec. 8, 2016, pp. 1-10.

* cited by examiner

ELECTRONIC SENSOR SYSTEM FOR USE WITH FOOTWEAR

CLAIM FOR PRIORITY

This application claims the benefit of U.S. Provisional Application No. 62/199,818 of the same title and filed on Jul. 31, 2015, which is incorporated by reference herein.

TECHNICAL FIELD

The technique introduced here relates to the field of electronic sensor systems for footwear.

BACKGROUND

The use of orthotic inserts in footwear to assist in the therapy and alignment of the wearer's neuromuscular and skeletal systems is known. One refinement to such orthotics contemplates their use in combination with electronic pressure sensors so that the wearer can be assessed and/or monitored.

SUMMARY

Disclosed herein is an orthotic insert configured with an improved electronic sensor layer that provides feedback on important information regarding the wearer's gait mechanics (such as the force and pressure distribution on substantially the complete footprint of the wearer) during walking and other physical activities. The layer of sensors is used to assist in monitoring the wearer's health via foot pressure tracking.

Known existing sensing systems for footwear to date are limited to 8 sensors; in other words, the force/pressure signals from no more than 8 sensors (distributed around the wearer's foot) can be tracked. This is because the signals are processed through an analog-to-digital converter (ADC) device, and presently such ADC devices typically have an 8 channel limit. The technique introduced here is able to utilize 9 or more (substantially more, where appropriate) sensors on the sensor layer. At least one embodiment of the disclosed system incorporates the use of one or more 32-channel analog multiplexers (or multiplexer switches) and Bluetooth 4.0 low-energy technology (the latter being used to transmit/communicate the data), to significantly increase the number of sensors that can be handled. Using a large quantity of standardized sensors allows the sensor layer to be more readily customizable and robust to different foot and gait biomechanics.

Furthermore, existing sensing systems that are used with footwear are generally either impractically thick or not customizable. The manufacturing process disclosed, coupled with the selection of suitable sensors and materials, enables sensor layers having a thickness of less than 2.6 mm to be produced.

The technique introduced here relates to an insert for footwear and to a composite orthotic insole comprising said insert, wherein the insert (or sensor layer) is embedded with a plurality of force (or pressure) sensors, and may be used to gather the wearer's foot pressure data (such as gait biomechanics) during various physical activities. The insert can include 9 or more embedded sensors, which together will provide broad coverage and precise sensing of the human foot impact area. In at least one embodiment, the insert comprises a polydimethylsiloxane (PDMS) covering to seal and protect the layer of sensors, thus providing flexibility, durability and waterproofing of the insert. The applicable data collected from the sensors will be passed to a proximally-located, battery-powered microcontroller (which may be concealed within or beneath the orthotic insole, such as in the area of the foot arch) which can use standard Bluetooth (4.0) communications technology to communicate such data to external devices.

BRIEF DESCRIPTION OF THE DRAWINGS

Embodiments of teachings introduced here are described below with reference to the accompanying drawings in which.

DETAILED DESCRIPTION

Figure 1:
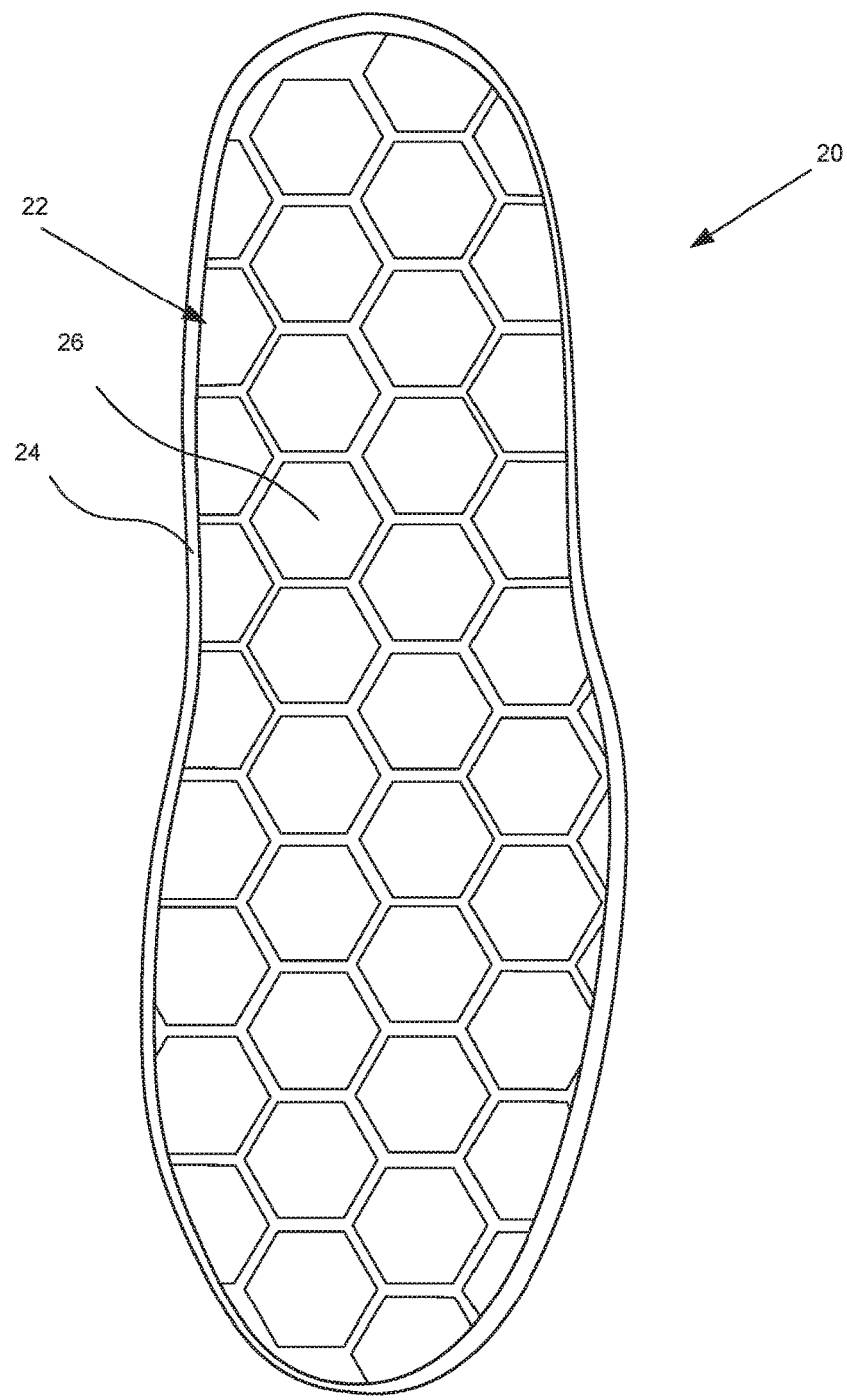
FIG. 1 is a simplified top view of the composite orthotic insole and sensor layer, illustrating the layout of the sensors in the sensor layer.

FIG. 1 is a simplified top view of the composite orthotic insole and sensor layer, illustrating the layout of the sensors in the sensor layer. A schematic top view of a smart orthotic insert 20 is shown. The orthotic insert 20 includes a number of layers. Displayed is a sensor layer 22 and a surface layer 24 which the sensor layer is placed on top of. The surface layer 24 would go around the exterior of the orthotic insert 20 and is the surface upon which users contact with their feet. The sensor layer 22 is generally in the shape of a wearer's foot, and is made up of a plurality of electronic pressure or force sensors 26 wired together in a network. The sensor 26 themselves may merely be conductive contacts that make up a portion of a pressure sensor or switch. The surface layer 30 serves to completely seal and protect the sensor layer (among other layers), and may be made from a material such as PDMS, or other suitable plastics or gel materials which are flexible, durable and waterproof.

Each of the active sensors 26 is shown as having a hexagonal shape (although it should be understood that other shapes of sensors are also possible, such as circular). The general layout of the sensors 26 in relation to a wearer's foot shape is shown in FIG. 1. The number of sensors 26 and their placement/coverage around the shape of the foot is such that all important areas of the foot will be measured, regardless of the wearer's foot shape specifics, as well as regardless of the wearer's gait mechanic changes during the orthotic lifetime.

An embodiment of the technique introduced here is described herein in the form of a sensor layer 22 of an orthotic insert 10. However, it should be understood that the sensor layer could instead be used in combination with a regular insole or insert, or by itself as an insert for footwear.

Figure 2:
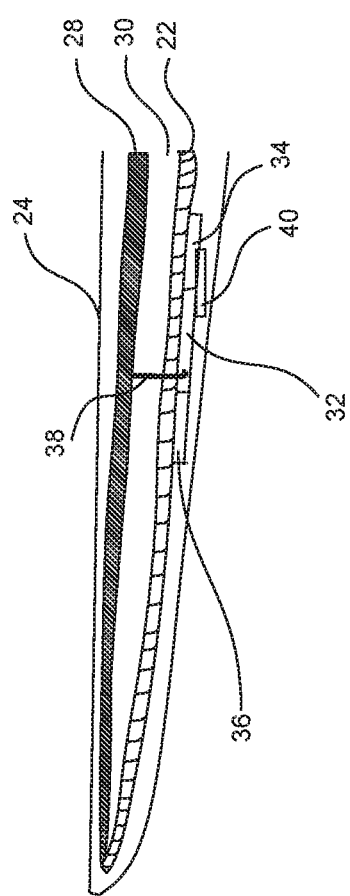
FIG. 2 is a cross-sectional view of an embodiment of an orthotic insole having multiple layers.

FIG. 2 is a cross-sectional view of an embodiment of an orthotic insole having a number of layers. The sensor layer 22 interacts with a number of layers, including a pressure-sensitive resistor layer ("PSR layer") 28. The PSR 28 may comprise a layer of Velostat as manufactured by the 3M Company. Other materials are suitable so long as the material used has a variable electrical resistance which is controlled by the amount of pressure applied to the material. The electrical resistance is reduced when pressure is applied. Between the sensor layer 22 and the pressure-sensitive resistor layer 28 is an air gap layer 30. The air gap layer 30 is established through the structure of the surface layer 24 which keeps the PSR layer 28 and the sensor layer 22 split apart. After the orthotic insert 20 is constructed, the air pressure of the air gap layer 30 maintains the integrity of the air gap layer 30.

Below the sensor layer 22 are electronic components. The electronic components include a microcontroller 32, and a wireless communicator 34. Optionally a multiplexer 36 is connected to the microcontroller 32. The sensors 26 are connected to either the microcontroller 32 or the multiplexer 36. There is also a differential contact 38 that runs between the microcontroller 32 and the PSR layer 28 that completes the circuit. The circuit is powered by a battery 40. The battery 40 may be rechargeable or replaceable.

The general functionality of the layers is as follows. The differential contact 38 carries the voltage difference from the battery 40 to the PSR layer 28. The PSR layer 28 changes its resistance when bent, compressed or is otherwise deformed by external forces (in this case, foot impact). The air gap layer 30 is placed below the PSR layer 28 to provide cushioning and support for the PSR layer 28, and therefore regulate how much pressure is required to alter the shape of the PSR layer 28. In other words, The air gap layer 30 regulates how much force or pressure is required to create the resistance difference in the circuit. Where the PSR layer 28 contacts the sensor layer 22 (the particular sensors 26) a circuit is completed. The changing resistance is measured in the microcontroller 32, and converted into digital data points for software interpretation. The recorded voltage enables calculation of the magnitude of pressure applied to the sensor as well as the timing for the applied pressure.

Based on the number of sensors 26, the orthotic insert 20 makes use of the multiplexer 36. Where the microcontroller 32 is configured to accept all of the inputs on the of the sensors 26 directly, no multiplexer 36 is required. Where the number of sensors 26 is greater than the number of sensor inputs on the microcontroller 32, a multiplexer 36 enables additional sensor input to the microcontroller 32. In at least one embodiment, the sensor coverage will be such that a minimum of nine sensors 26 providing pressure data points at all times.

In at least one embodiment, the complete pressure sensors are composed of a Velostat™ layer, an air gap layer, sensor layer and electronic components. Sensors 26 can be sized as desired, possibly in the 5 mm to 40 mm range. The sensors are semi-custom, in that the sensors 26 are based on a standard set of layers, and customized in terms of shape and size to fit the design of the sensor sheet. An example of a suitable off-the-shelf complete pressure sensor that utilizes a usable pressure-sensor configuration is the Teksan™ Flexi-Force™ A201.

The sensor sheet can be used in contact with a human foot and placed above an orthotic insert (which itself is preferably one that has been customized to a shape or profile to provide the wearer with specific biomechanical improvements). The sensor layer can provide gait and stride force/pressure feedback to validate these improvements, and predict future orthotic refinements. The gathered data could be used for performance analysis, performance improvement recommendation, health tracking, injury prevention, and various other biomechanical applications.

Figure 3:
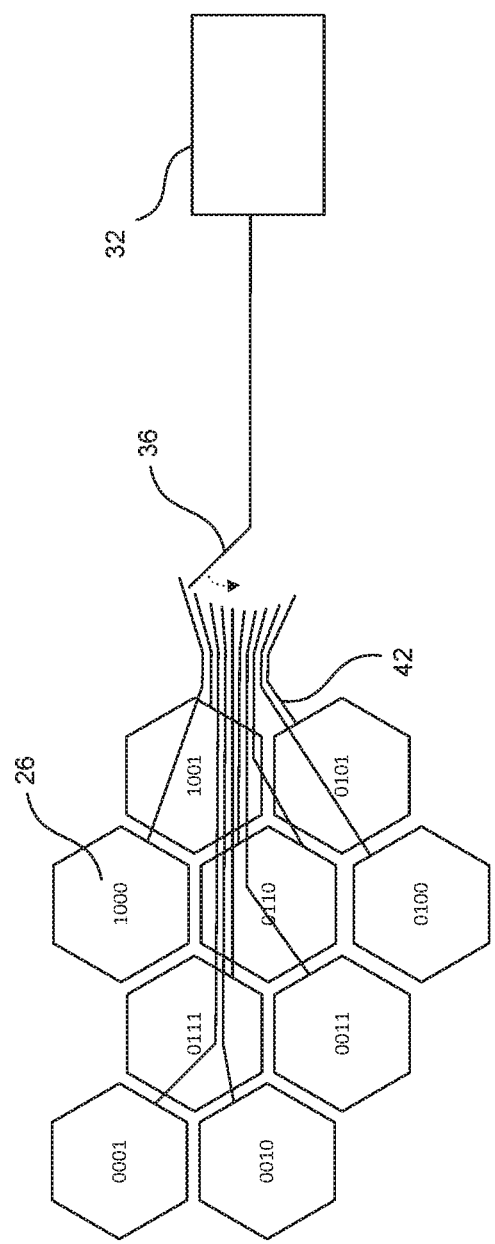
FIG. 3 is a schematic diagram illustrating the wiring for the sensors in the sensor layer and illustrating the multiplexer function.

FIG. 3 is a schematic diagram illustrating the wiring for the sensors 26 in the sensor layer 22 and illustrating the multiplexer 36 function. The schematic diagram illustrates the wiring 42 of nine separate sensors 26 and the multiplexer 36 function. To enable 9+ channels of data logging, one or more multiplexer switches 36 is used.

The sensors are wired through one or more multiplexer switch 36, which can be analog 32-channel switches, for example. From the multiplexer switch 36, the wiring 42 runs to a microcontroller 32, which is limited to 8 inputs. It may be preferable that a particular sensor sheet be made up of sensors 26 that are standardized and the same size, since this makes the sensor sheet more readily customizable and facilitates comparisons (and provides for uniformity) of the various sensor signals from the same foot or from different wearers; however, sensors 26 of differing sizes could be used.

The multiplexer 36 will switch between the sensors 26 rapidly, i.e., fast enough to ensure that any measurable pressure changes can be detected and recorded. The multiplexer 36 switches one of multiple inputs to the common output, determined by a unique binary address lines (samples are marked on each sensor 26).

For 9-16 sensors, a 16-channel analog multiplexer can be used, switching one of 16 inputs to one, determined by four-bit binary address lines (in this case, a 32-channel analog multiplexer could also be used). For 17-32 sensors, a 32-channel analogy multiplexer can be used, switching one of 32 inputs to one, determined by five-bit binary address lines. Alternatively, where appropriate, two or more multiplexers 36 can be used in combination. The signal from the sensors is passed to a microcontroller 32, which can include a microcontroller and associated electronic equipment (including battery unit and communication hardware).

The above-described approach involving relatively large numbers of sensors is practical in combination with the use of electronics that consume small amounts of power (such as low-power sensors) and that require low-power for communication through the wireless communicator 34. Bluetooth 4.0 standard technology, compatible with iBeacon™, for example, can be used to conserve battery life. Other forms of wireless communicators 34 are also suitable such as WiFi or cellular (GSM, CDMA, GPRS, etc . . . ) so long as the wireless communicator 34 is compact.

Figure 4:
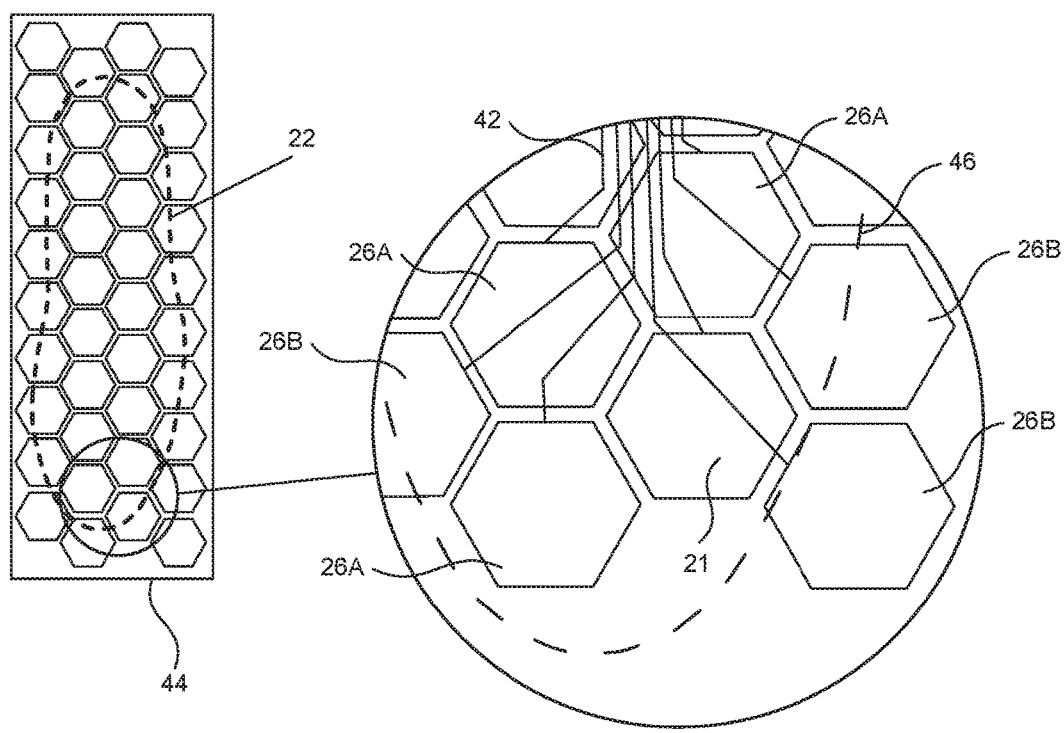
FIG. 4 is a top view of the sensor sheet, along with an enlarged fragmentary view of a section thereof, illustrating the wiring of the sensors.

FIG. 4 is a top view of a sensor sheet 44, along with an enlarged fragmentary view of a section thereof, illustrating the wiring 42 of the sensors 26. The sensor sheet 44 itself can be designed to allow trimming and customizing for each unique footprint. The sensors 26A and peripheral sensors 26B are placed and wired in such a way that the electrical wires 42 are directed generally towards the center of the basic foot shape. This enables adding or subtracting to the sensor sheet 44 design without disrupting the wiring 42 of the sensor 26. This also provides the advantage of being able to trim/customize each sheet to a specific foot shape, by cutting through some of the peripheral sensors 26B, without significantly affecting the functionality of the sensor layer 26 as a whole. In FIG. 4, the trim line 46 for the sensor layer 22 for a particular foot-size indicates that certain peripheral sensors 26B will be compromised by the trimming and would not function; other active sensors 26A; however would continue to be able to record pressure data.

The production process can start with a set of standard sensor sheets 44. In some embodiments these sensor sheets 44 are categorized for one or more shoe sizes. In some embodiments, the sensor sheets 44 are suitably large to be used for all shoe sizes. The customization of the orthotic inserts 20 begins with the sizing of the sensor sheet 44. Where customized foot sized data is received by the manufacturer, a very particular foot shape may be cut into the sensor sheet 44 matching foot of the intended user as accurately as possible. This is technique is highly customizable, in part, as a result of the repeating, pattern of the sensors 26 on the sensor sheet 44, and that the wiring 42 for each of the sensors 26 is routed towards the center of the sensor sheet 44. Routing the wiring 42 to the center of the sensor sheet 44 enables large variation in the foot size cut 46 into the sensor sheet 44 while still enabling the wiring 42 to function for all remaining sensors 26.

Figures 5A, 5B:
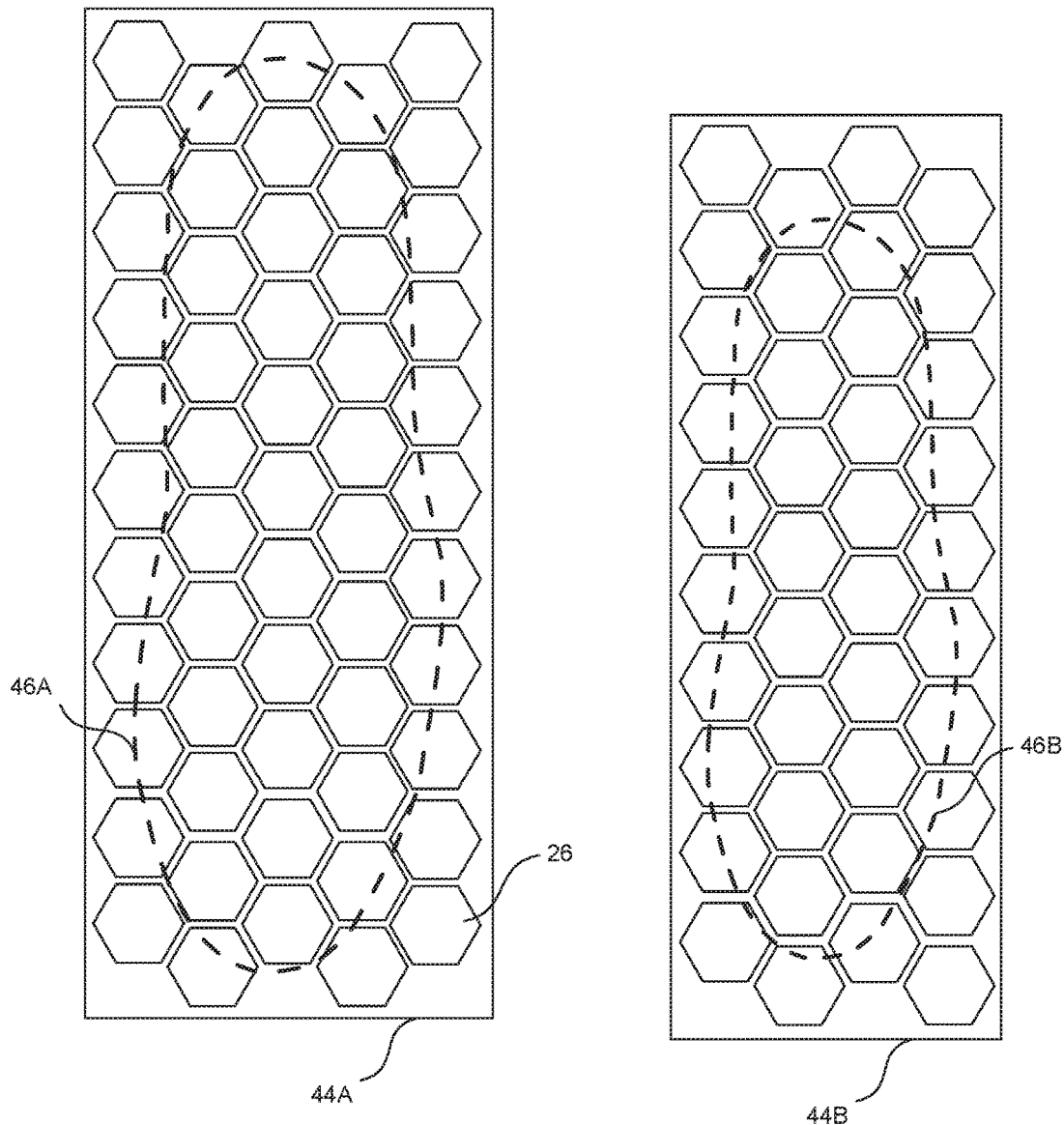
FIGS. 5A and 5B are a simplified diagram (top view) of two differently sized sensor sheets, illustrating how each can be trimmed to form a sensor layer for different-sized feet.

This is illustrated in FIGS. 5A and 5B, which show two differently sized sensor sheets 44A and 44B, and illustrate how each could be trimmed to be formed into a sensor layer for two different-sized feet (in this case, sensor sheet 44A for a relatively larger foot, and sensor sheet 44B for a relatively smaller foot). It also may be preferable that the sensor sheet 44 be made relatively thin—in practice, a thickness of less than about 2.6 mm may be considered optimal.

The optimal sized sheet is chosen, then trimmed/customized along the trim lines 46A and 46B respectively for the individual foot shape. Each standard sheet size could be produced in bulk using a packaging machine, or produced using additive manufacturing with a modified 3D printer. It also may be preferred to determine sensor spacing based on foot size. For example, relatively smaller foot sizes may require less spacing between sensors than larger sizes. In cases where a standardized sensor sheet 44 is used, there is a positive correlation between a number of sensors 26 to the foot size trim lines 46. Further, in those embodiments there is a static density of sensors 26 despite variance to the foot size trim lines 46.

Figure 6:
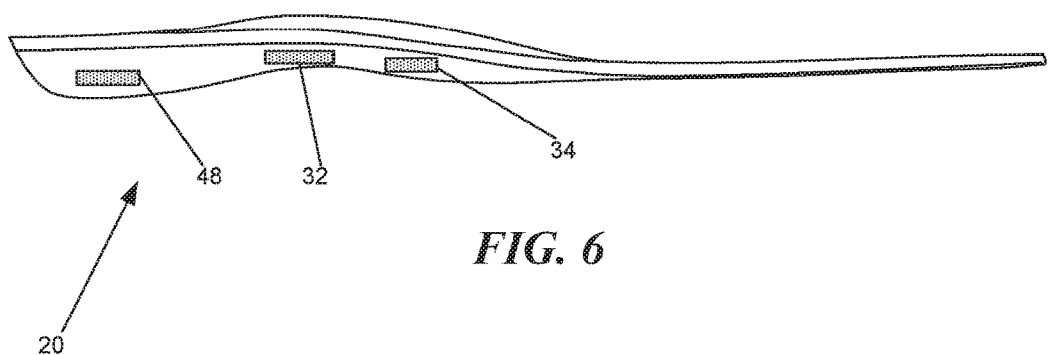
FIG. 6 is a side view of an embodiment of an orthotic insole including a number of electronic components.

FIG. 6 is a side view of an embodiment of an orthotic insole including a number of electronic components. In addition to a set of pressure sensors 26, additional instruments 48 can be inserted in the orthotic insert 20 to provide data. The additional instruments 48 may include, for example: a geolocation sensor (such as a GPS), a thermometer, an accelerometer, an ultrasonic sensor, a heartbeat sensor and/or a gyroscope. More than one of the additional instruments 48 may be placed within the orthotic insert 20. The additional instruments feed collected data to the microcontroller 32 which in turn feeds data to the wireless communicator 34 for transmission. The additional instruments 48 provide additional data that help shape the machine understood story of the travel a foot, a pair of feet, or even a whole body take.

In some embodiments, the additional instruments 48 are socketed into an insole without the pressure sensors. Rather than use a layered pressure sensor, the additional instruments 48 are inserted into sockets in the surface layer 24. Between the sockets wiring connects the microcontroller 32 and the wireless communicator 34 and the battery 40.

Figure 7:
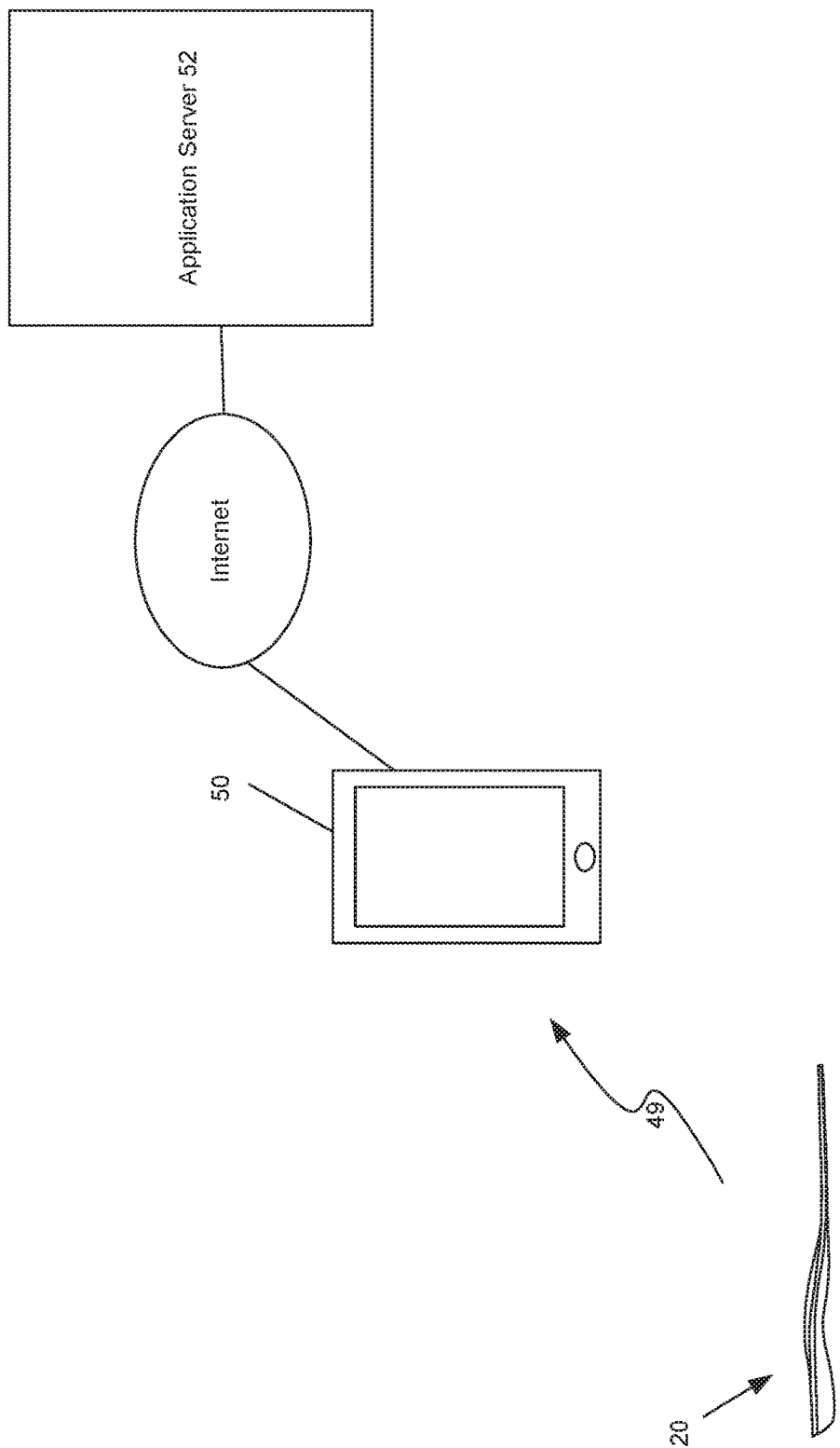
FIG. 7 is a block diagram of a system including an external user device and an application server.

FIG. 7 is a block diagram of a system including an external user device and an application server. The orthotic insert 20 uses the internal wireless communicator 34 to transmit data and signals 49 collected and processed by the microcontroller 32 to an external device 50. The external device 50, may be a number of devices including but not limited to a smart phone, a tablet, a laptop or desktop computer, a virtual reality interface, a augmented reality interface, and a suitable control module known in the art.

Processed data and signals 49 are either used directly by the external device 50, or forwarded to an applications server 52. The external device 50 may be connected to the application server 52 through wireless, network, or wired connections. In some embodiments, the processed data and signals 49 are used to construct analytical models of the wearer's gait, physical stresses, and body health.

Another possible application for the disclosed system is for entertainment purposes. For example, the foot pressure on the wearer may be tracked through the layer of sensors and used as inputs to a connected user-interactive processing device (such as a video game system or a virtual reality hardware device). The wearer can provide instructions to or otherwise control the processing device, at least in part, via the foot pressure communicated (e.g. the wearer may represent/simulate actions such as jumping, walking, hopping, balancing, etc.).

Figure 8:
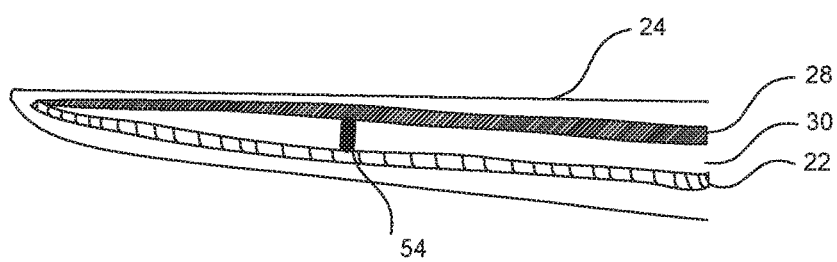
FIG. 8 is a cross-sectional view of an embodiment of an orthotic insole having a support pillar in an air gap layer.

FIG. 8 is a cross-sectional view of an embodiment of an orthotic insole 20 having a support pillar 54 in an air gap layer 30. In order to increase the resistance of the air layer 30 beyond air pressure, one or more collapsible support pillars 54 or substrate may be affixed within the air gap layer 30 increasing the amount of pressure required upon the PSR layer 38 in order to make contact with the sensor layer 22.

Figure 9:
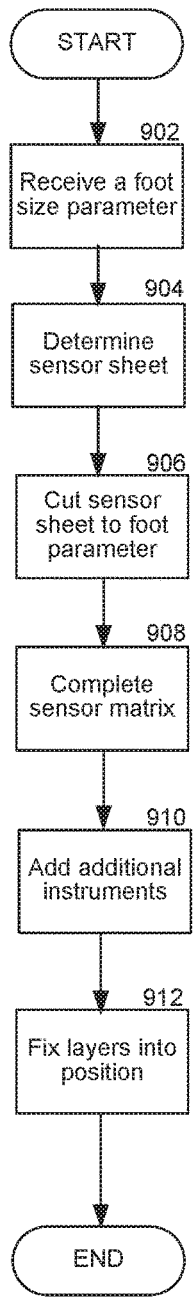
FIG. 9 is a flowchart of a method for customization of an orthotic insole.

FIG. 9 is a flowchart of a method for customization of an orthotic insole. In step 902, a insole manufacturing station receives foot size parameters. The scope of insole manufacturing station is general. Included examples of a insole manufacturing station are a corporate entity with the purpose of manufacturing insoles, a 3D printer, a single machine that assembles insoles, or a group of machines that assemble insoles. The foot size parameters pertain to the size of a customer's foot as measured by an external method. In step 904, the insole manufacturing station determines the correct sensor sheet 44 to use for the particular customer's foot size parameter.

In step 906, the insole manufacturing station cuts the sensor sheet to the foot size parameter. In doing so, extraneous sensors 26B and wiring 42 for those sensors are stripped away leaving only the sensors 26A which will remain in the sensor layer 22. In step 908, the remainder of the sensor matrix is completed: the PSR layer 28 and the air gap layer 30 are formed. The electronic components (microcontroller 32, multiplexer 36, and wireless communicator 34) are connected to the wiring 42 and the differential contact 38 is connected to the PSR layer 28.

In step 910, any additional instruments 48 are added as suitable. In step 912, the layers, including the surface layer 24 are fixed into positon and a completed custom orthotic insert 20 is ready to ship to the customer.

Figure 10:
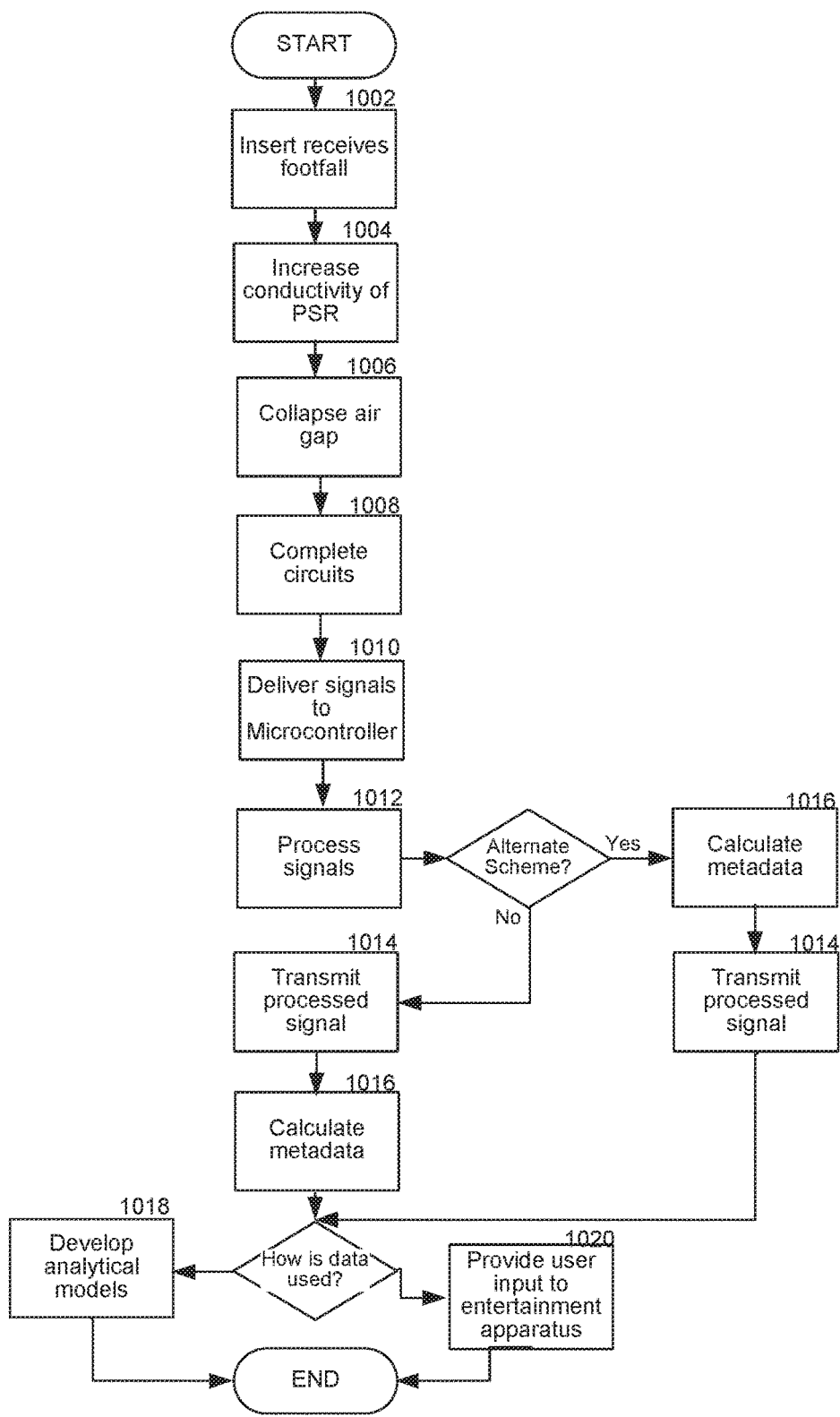
FIG. 10 is a flowchart of a method of receipt and transmission of signals from an orthotic insert.

FIG. 10 is a flowchart of a method of receipt and transmission of signals from an orthotic insert. In step 1002, the orthotic insert 20 receives a footfall, the footfall imparting pressure upon the insert 20. In step 1004, the imparted pressure increasing the conductivity of the PSR layer 28 of the insole 20. In step 1006, the imparted pressure further causes the air gap layer 30 to at least partially collapse. The collapse of the air gap layer 30 causes the PSR layer 28 to contact one or more sensors 26 on a sensors layer 22 of the insert 20.

In step 1008, the orthotic insert 20 completes one or more circuits between the one or more sensors 26 and the PSR layer 28. In step 1010, each completed circuit delivers a signal to a microcontroller 32, each signal including a unique identifier associated with each of the one or more sensors that complete the one or more circuits. In inserts 20 with a multiplexer 36 the unique identifier is determined by a binary code corresponding to the input on the multiplexer 36. In inserts 20 without a multiplexer, the unique identifier is indicated by the input used on the microcontroller 32.

In step 1012, the microcontroller 32 processes the received signals. In step 1014, the microcontroller 32 delivers the processed signals to the wireless communicator 34 for transmission. In step 1016, the signals are analyzed with a measured voltage to determine the magnitude of the pressure supplied by the footfall across each sensor 26 receiving pressure. Step 1016 may be performed either by the microcontroller 32 prior to step 1014, or after step 1014 by an external device 50 or an application server 52.

Depending on how the transmitted data is to be used by the external device 50 or application server 52, the method proceeds to step 1018 or 1020. In step 1018, the external device 50 or application server 52 uses the transmitted signals to develop analytical models of footfalls. In step 1020, the transmitted signals provide user input to an entertainment apparatus such as a game system or virtual/augmented reality apparatus.

The embodiments described herein are not, and are not intended to be, limiting in any sense. One of ordinary skill in the art will recognize that the disclosed technique(s) may be practiced with various modifications and alterations, such as structural and logical modifications. Although particular features of the disclosed technique(s) may be described with reference to one or more particular embodiments and/or drawings, it should be understood that such features are not limited to usage in the one or more particular embodiments or drawings with reference to which they are described, unless expressly specified otherwise.

The invention claimed is:

1. A flexible, multi-layered insole for footwear, the insole comprising:
   a surface layer to contact a foot of a user;
   a pressure-sensitive resistor layer having an electrical resistance that varies based upon applied pressure, wherein applied pressure reduces resistance to electrical current passing from a first side of the pressure-sensitive resistor layer to a second side of the pressure-sensitive resistor layer that is opposite the first side;
   a sensor including a plurality of sensors arranged laterally across the insole, each sensor having a unique identifier;
   an air gap between the pressure-sensitive resistor layer and the sensor layer, the air gap configured to collapse at least partially when the insole receives a footfall to thereby cause contact between the pressure-sensitive resistor layer and one or more of the sensors and cause each of said one or more of the sensors to output a respective signal including a respective unique identifier;
   a load column positioned within the air gap and affixed between the pressure-sensitive resistor layer and the sensor layer, wherein the load column regulates an amount of pressure required to collapse the air gap, and wherein a largest dimension of the load column is perpendicular to a largest dimension of the flexible, multi-layered insole; and
   a microcontroller coupled to receive and process the respective signals from the sensors wherein the microcontroller identifies sensor of origin of the one or more sensors based on the respective unique identifier included in each respective signal.

2. The insole of claim 1, further comprising:
   a wireless communicator communicatively coupled with the microcontroller and configured to transmit processed signals from the microcontroller an external device.

3. The insole of claim 1, further comprising:
   a multiplexer to receive the signals from the sensors and selectively output a subset of the signal to the microcontroller.

4. The insole of claim 1, wherein each of the sensors of the sensor layer includes a contact that directs the corresponding to a central location on the insole.

5. The insole of claim 4, wherein the central location is an arch section of the insole.

6. The insole of claim 1, wherein the sensors are arranged in a repeating pattern across the sensor layer.

7. The insole of claim 6, wherein the sensor layer contains a positive correlation between a number of sensors to a foot size of insole, and a static density of sensors despite variance in the foot size of insole.

8. The insole of claim 1, further comprising one or more of:
   a geolocation sensor;
   a thermometer;
   an accelerometer;
   an ultrasonic sensor;
   a heartbeat sensor; or
   a gyroscope.

9. The insole of claim 2, further comprising:
   application software resident on the external device, the application software including instructions to receive signals transmitted from the wireless communicator and develop analytical footfall models to report to a user.

10. The insole of claim 2, further comprising:
    application software resident on the external device, wherein the external device is a gaming apparatus, and the application software including instructions to receive signals transmitted from the wireless communicator and provide user inputs to the gaming apparatus thereby influencing virtual reality simulations.

11. A method comprising:
    receiving a footfall on a flexible, multi-layered insole, the footfall imparting pressure upon the insole;
    in response to the imparted pressure, increasing the conductivity of a first layer of material of the insole, wherein resistance to electrical current passing from a first side of the first layer to a second side of the first layer that is opposite to the first side is reduced;
    causing the first layer to at least partially collapse an air gap and contact one or more sensors included in a second layer of the insole, wherein the air gap is supported by a load column positioned within the air gap and affixed between the first layer and the second layer, the load column regulates an amount of pressure required to collapse the air gap, wherein a largest dimension of the load column is perpendicular to a largest dimension of the flexible, multi-layered insole; and
    completing one or more circuits between the one or more sensors of the second layer and the first layer, each completed circuit delivering a signal to a microcontroller, each signal including a unique identifier associated with each of the one or more sensors that complete the one or more circuits.

12. The method of claim 11, further comprising:
transmitting, by a wireless communicator, processed signals from the microcontroller to an external device.

13. The insole system of claim 11, further comprising:
cutting the sensor layer to a custom insole size from a sheet of sensors having a repeating pattern of sensors, each of the sensors including a contact directed to the center of the sheet of sensors such that contacts meet at a location on the sensor sheet which is included in every cut sensor layer despite variance in insole size.

14. The method of claim 13, wherein the sensor layer contains a positive correlation between a number of sensors to a foot size of insole, and a static density of sensors despite variance in the foot size of insole.

15. The method of claim 12, wherein the transmitting step further includes transmitting data from integrated sensors, integrated sensors further comprising one or more of the following sensors:
a geolocation sensor;
a thermometer;
an accelerometer;
an ultrasonic sensor;
a heartbeat sensor; or
a gyroscope.

16. The method of claim 12, further comprising:
receiving, by application software resident on the external device, signals transmitted from the wireless communicator; and
developing analytical footfall models to report to a user.

17. The method of claim 12, further comprising:
receiving, by application software resident on the external device, signals transmitted from the wireless communicator, wherein the external device is an entertainment apparatus; and
providing user inputs to the entertainment apparatus thereby influencing virtual reality simulations.

18. A flexible, multi-layered insole for footwear, the insole comprising:
a surface arranged to contact a foot of a user;
a pressure-sensitive resistor layer that becomes more conductive as pressure is applied;
a sensor layer including a plurality of sensors arranged laterally across the insole, each sensor having a unique identifier;
an air gap between the pressure-sensitive resistor layer and the sensor layer, the air gap configured to collapse at least partially when the insole receives a footfall to thereby cause contact between the pressure-sensitive resistor layer and one or more of the sensors and cause each of said one or more of the sensors to output a respective signal including a respective unique identifier;
a buckling load column positioned within the air gap and affixed between the pressure-sensitive resistor layer and the sensor layer that regulates the amount of pressure required to collapse the air gap; and
a microcontroller coupled to receive and process the respective signals from the sensors wherein the microcontroller identifies sensor of origin of the one or more sensors based on the respective unique identifier included in each respective signal.

19. The insole of claim 18, further comprising:
a wireless communicator communicatively coupled with the microcontroller and configured to transmit processed signals from the microcontroller an external device.

20. The insole of claim 18, further comprising:
a multiplexer to receive the signals from the sensors and selectively output a subset of the signal to the microcontroller.

21. The insole of claim 18, wherein each of the sensors of the sensor layer includes a contact that directs the corresponding to a central location on the insole.

22. The insole of claim 21, wherein the central location is an arch section of the insole.

23. The insole of claim 18, wherein the sensors are arranged in a repeating pattern across the sensor layer.

24. The insole of claim 14, wherein the sensor layer contains a positive correlation between a number of sensors to a foot size of insole, and a static density of sensors despite variance in the foot size of insole.

25. The insole of claim 18, further comprising one or more of:
a geolocation sensor;
a thermometer;
an accelerometer;
an ultrasonic sensor;
a heartbeat sensor; or
a gyroscope.

* * * * *